(12) United States Patent
Minagawa et al.

(10) Patent No.: US 11,614,440 B2
(45) Date of Patent: Mar. 28, 2023

(54) SPECIFIC CELL FRACTIONATING AND CAPTURING METHODS

(71) Applicants: SUMITOMO RUBBER INDUSTRIES, LTD., Kobe (JP); YAMAGATA UNIVERSITY, Yamagata (JP)

(72) Inventors: Yasuhisa Minagawa, Kobe (JP); Masaru Tanaka, Yonezawa (JP); Haruka Emura, Yonezawa (JP); Kazuki Suto, Yonezawa (JP)

(73) Assignees: SUMITOMO RUBBER INDUSTRIES, LTD., Kobe (JP); YAMAGATA UNIVERSITY, Yamagata (JP)

( * ) Notice: Subject to any disclaimer, the term of this patent is extended or adjusted under 35 U.S.C. 154(b) by 629 days.

(21) Appl. No.: 16/728,731

(22) Filed: Dec. 27, 2019

(65) Prior Publication Data

US 2020/0238201 A1 Jul. 30, 2020

(30) Foreign Application Priority Data

Jan. 24, 2019 (JP) .............................. JP2019-010400
Apr. 23, 2019 (JP) .............................. JP2019-082074

(51) Int. Cl.
*G01N 33/50* (2006.01)
*B01J 20/26* (2006.01)
*G01N 33/49* (2006.01)

(52) U.S. Cl.
CPC ........ *G01N 33/5002* (2013.01); *B01J 20/261* (2013.01); *G01N 33/491* (2013.01); *G01N 33/5094* (2013.01)

(58) Field of Classification Search
CPC ........... G01N 2030/528; G01N 30/482; G01N 30/603; G01N 33/491; G01N 33/5002;
(Continued)

(56) References Cited

U.S. PATENT DOCUMENTS 3,902,964 A * 9/1975 Greenspan ......... G01N 33/5002
435/13
5,202,025 A   4/1993 Onishi et al.
(Continued)

FOREIGN PATENT DOCUMENTS

CN   104039949 A   9/2014
CN   105263995 A   1/2016
(Continued)

OTHER PUBLICATIONS

"Improved Recovery of Cell-Derived Exosomes by MPC Polymer Coatings," Nippon Genetics Co., Ltd, vol. 9, 2018, with a concise explanation of the relevance.
(Continued)

*Primary Examiner* — Michael P Stafira
(74) *Attorney, Agent, or Firm* — Birch, Stewart, Kolasch & Birch, LLP

(57) ABSTRACT

Provided are specific cell-fractionating and -capturing methods which can fractionate and capture, respectively, specific cells (e.g., many types of cancer cells, including cancer cells not expressing EpCAM, or peripheral blood stem cells). Included is a method for fractionating specific cells present in blood or biological fluid, the method including fractionating the blood or biological fluid by centrifugation to collect the specific cells in the blood or biological fluid, the centrifugation being carried out using a container having a low protein adsorbing layer at least partially formed on the inner surface thereof.

27 Claims, 2 Drawing Sheets

(58) Field of Classification Search
CPC ............ G01N 33/5094; G01N 1/4077; G01N
2001/2846; G01N 27/20; G01N 27/24;
G01N 33/57492; G01N 2500/00; G01N
33/68; G01N 33/54386; G01N 33/574;
G01N 33/6803; G01N 33/6848; G01N
33/48721; G01N 2333/70596; G01N
27/44743; G01N 33/6806; G01N 21/78;
G01N 2333/78; G01N 2800/52; G01N
2333/471; G01N 2800/36; G01N
2800/368; G01N 33/53; G01N 33/564;
G01N 33/57476; G01N 33/6887; G01N
33/689; G01N 27/447; G01N 33/57484;
G01N 33/57426; G01N 33/15; G01N
33/487; G01N 33/60; G01N 33/5011;
G01N 2500/02; G01N 2500/04; G01N
2800/062; G01N 33/5041; G01N 33/577;
G01N 33/6845; G01N 33/6866; G01N
33/6869; G01N 2030/884; G01N
2333/49; G01N 2400/00; G01N 30/88;
G01N 33/6812; G01N 33/543; G01N
33/5436; G01N 33/567; G01N
2030/8831; G01N 2333/705; G01N
33/50; G01N 33/5088; G01N 33/57449;
G01N 2333/21; G01N 2800/00; G01N
2800/342; G01N 33/505; G01N 33/566;
G01N 33/56911; G01N 33/6842; G01N
27/26; G01N 2800/06; G01N 2800/26;
G01N 2800/7028; G01N 33/5308; G01N
33/534; G01N 33/542; G01N 33/54313;
G01N 33/57407; G01N 33/57423; G01N
33/66; G01N 33/6818; G01N 2333/7051;
G01N 2333/70514; G01N 2333/70517;
G01N 2333/71; G01N 2333/1194; G01N
2400/40; G01N 27/44704; G01N
27/44721; G01N 27/44726; G01N
27/44747; G01N 27/44782; G01N
27/44791; G01N 33/54306; G01N
33/561; G01N 33/56972; G01N
33/56977; G01N 33/57415; G01N
33/57442; G01N 33/57488; G01N
33/6854; G01N 33/6857; G01N 33/6878;
G01N 33/6893; G01N 1/405; G01N
15/0205; G01N 15/1404; G01N 15/1459;
G01N 15/1484; G01N 2015/0288; G01N
2015/0294; G01N 2015/1006; G01N
2015/149; G01N 2015/1493; G01N
2015/1497; G01N 2030/027; G01N
21/65; G01N 2333/51; G01N
2333/70539; G01N 2333/70578; G01N
2333/90633; G01N 2333/96494; G01N
2570/00; G01N 2800/24; G01N
2800/7042; G01N 33/02; G01N
33/48707; G01N 33/5014; G01N
33/5064; G01N 33/54326; G01N 33/544;
G01N 33/57438; G01N 33/582; G01N
33/6863; B01J 20/06; B01J 20/08; B01J
20/103; B01J 20/28004; B01J 20/28019;
B01J 20/28042; B01J 20/283; B01J
20/3007; B01J 20/3042; B01J 20/3078;
B01J 20/3085; B01J 20/3204; B01J
20/3236; B01J 20/3289; B01J 20/3293;
B01J 20/3295; B01J 20/261
See application file for complete search history.

(56) References Cited

U.S. PATENT DOCUMENTS

| | | | |
|---|---|---|---|
| 5,660,798 A * | 8/1997 | Doshi | G01N 33/5002 |
| | | | 436/526 |
| 7,211,433 B1 | 5/2007 | Dahm et al. | |
| 9,372,136 B2 * | 6/2016 | Kanbara | G01N 1/405 |
| 9,709,556 B2 * | 7/2017 | Idelevich | G01N 33/57492 |
| 10,941,374 B2 * | 3/2021 | Minagawa | B01L 3/5085 |
| 2002/0155617 A1 | 10/2002 | Pham et al. | |
| 2003/0190405 A1 | 10/2003 | Bowers et al. | |
| 2006/0008807 A1 | 1/2006 | O'Hara et al. | |
| 2006/0160066 A1 | 7/2006 | Bhatia et al. | |
| 2007/0099207 A1 | 5/2007 | Fuchs et al. | |
| 2008/0008736 A1 | 1/2008 | Glauser | |
| 2008/0038841 A1 | 2/2008 | Ezoe et al. | |
| 2009/0186341 A1 | 7/2009 | Dahm | |
| 2010/0261159 A1 | 10/2010 | Hess et al. | |
| 2011/0123414 A1 | 5/2011 | Ahern et al. | |
| 2012/0077246 A1 | 3/2012 | Hong et al. | |
| 2012/0108468 A1 | 5/2012 | Keselowsky et al. | |
| 2012/0156698 A1 | 6/2012 | Jendoubi | |
| 2013/0059288 A1 | 3/2013 | Dankbar et al. | |
| 2013/0071916 A1 | 3/2013 | Frutos et al. | |
| 2013/0072402 A1 | 3/2013 | Takamura et al. | |
| 2013/0210140 A1 | 8/2013 | Burns et al. | |
| 2014/0158604 A1 | 6/2014 | Chammas et al. | |
| 2014/0299539 A1 | 10/2014 | Takai et al. | |
| 2014/0335610 A1 | 11/2014 | Fukumori et al. | |
| 2015/0017221 A1 | 1/2015 | Hayashi et al. | |
| 2015/0285786 A1 | 10/2015 | Hahn et al. | |
| 2016/0011192 A1 | 1/2016 | Wagner | |
| 2016/0069861 A1 | 3/2016 | Santore et al. | |
| 2016/0116477 A1 | 4/2016 | Hoffmann et al. | |
| 2016/0122488 A1 | 5/2016 | Minagawa | |
| 2016/0136552 A1 | 5/2016 | Nakanishi et al. | |
| 2016/0168294 A1 | 6/2016 | Hayashi et al. | |
| 2016/0223521 A1 | 8/2016 | Okamoto et al. | |
| 2016/0291019 A1 | 10/2016 | Yoon et al. | |
| 2017/0113218 A1 | 4/2017 | Chen et al. | |
| 2017/0225166 A1 | 8/2017 | Toner et al. | |
| 2017/0267960 A1 | 9/2017 | Tsukada et al. | |
| 2017/0304823 A1 * | 10/2017 | Sparks | B01L 3/50215 |
| 2018/0087071 A1 * | 3/2018 | Minagawa | B01L 3/5085 |
| 2018/0088105 A1 * | 3/2018 | Minagawa | C08F 20/58 |
| 2018/0088106 A1 * | 3/2018 | Minagawa | G01N 33/5005 |
| 2018/0201892 A1 | 7/2018 | Gomi et al. | |
| 2019/0048113 A1 | 2/2019 | Hayashi et al. | |
| 2019/0054123 A1 | 2/2019 | Kanai et al. | |
| 2019/0170741 A1 | 6/2019 | Alix-Panabieres et al. | |
| 2019/0233555 A1 | 8/2019 | Minagawa et al. | |
| 2019/0250149 A1 | 8/2019 | Minagawa | |
| 2019/0250151 A1 | 8/2019 | Minagawa et al. | |
| 2020/0056137 A1 | 2/2020 | Anzai et al. | |
| 2020/0056138 A1 | 2/2020 | Anzai et al. | |
| 2020/0056154 A1 | 2/2020 | Anzai et al. | |
| 2020/0056155 A1 | 2/2020 | Anzai et al. | |

FOREIGN PATENT DOCUMENTS

| | | | | |
|---|---|---|---|---|
| CN | 105636615 A | | 6/2016 | |
| EP | 0 225 703 A2 | | 6/1987 | |
| EP | 1655354 A2 | | 5/2006 | |
| EP | 1693109 A1 | * | 8/2006 | .......... B01L 3/50215 |
| EP | 1 905 824 A1 | | 4/2008 | |
| EP | 2720039 A1 | | 4/2014 | |
| EP | 3 244 208 A1 | | 11/2017 | |
| EP | 3 301 444 A1 | | 4/2018 | |
| EP | 3301443 A1 | * | 4/2018 | ............ B01L 3/5085 |
| EP | 3 527 985 A1 | | 8/2019 | |
| EP | 3 527 986 A1 | | 8/2019 | |
| GB | 2472321 A | | 2/2011 | |
| JP | 2-10160 A | | 1/1990 | |
| JP | 3-110473 A | | 5/1991 | |
| JP | 7-83923 A | | 3/1995 | |
| JP | 2002-536635 A | | 10/2002 | |
| JP | 2003-501629 A | | 1/2003 | |

(56) References Cited

FOREIGN PATENT DOCUMENTS

| | | |
|---|---|---|
| JP | 2004-522937 A | 7/2004 |
| JP | 2005-82538 A | 3/2005 |
| JP | 2005-188987 A | 7/2005 |
| JP | 2005-523981 A | 8/2005 |
| JP | 2006-109757 A | 4/2006 |
| JP | 2007-78665 A | 3/2007 |
| JP | 2007-515654 A | 6/2007 |
| JP | 2007-256268 A | 10/2007 |
| JP | 2008-529541 A | 8/2008 |
| JP | 2010-509570 A | 3/2010 |
| JP | 2012-105579 A | 6/2012 |
| JP | 2012-522217 A | 9/2012 |
| JP | 2013-500496 A | 1/2013 |
| JP | 2013-174616 A | 9/2013 |
| JP | 2014-105159 A | 6/2014 |
| JP | 2015-514396 A | 5/2015 |
| JP | 2015-224332 A | 12/2015 |
| JP | 2016-514950 A | 5/2016 |
| JP | 2016-131561 A | 7/2016 |
| JP | 2018-168019 A | 9/2016 |
| JP | 2017-83247 A | 5/2017 |
| JP | 2017-116511 A | 6/2017 |
| JP | 2017-523431 A | 8/2017 |
| JP | 2017-181096 A | 10/2017 |
| JP | 2018-59901 A | 4/2018 |
| RU | 2477981 C2 * | 3/2013 |
| WO | WO 99/42608 A1 | 8/1999 |
| WO | WO-0020921 A1 * | 4/2000 ............. B01J 13/02 |
| WO | WO 00/73794 A2 | 12/2000 |
| WO | WO 02/20825 A1 | 3/2002 |
| WO | WO 03/093357 A1 | 11/2003 |
| WO | WO 2005/064347 A1 | 7/2005 |
| WO | WO 2006/108087 A2 | 10/2006 |
| WO | WO 2007/092028 A2 | 8/2007 |
| WO | WO 2008/057437 A2 | 5/2008 |
| WO | WO 2019/111388 A2 | 9/2010 |
| WO | WO 2011/017094 A2 | 2/2011 |
| WO | WO 2011/157805 A1 | 12/2011 |
| WO | WO 2011/161480 A | 12/2011 |
| WO | WO 2012/108087 A1 | 8/2012 |
| WO | WO 2013/112541 A2 | 8/2013 |
| WO | WO 2013/134788 A1 | 9/2013 |
| WO | WO 2014/117021 A2 | 7/2014 |
| WO | WO 2014/203668 A1 | 12/2014 |
| WO | WO 2015/012315 A1 | 1/2015 |
| WO | WO 2015/046557 A1 | 4/2015 |
| WO | WO 2015/137259 A1 | 9/2015 |
| WO | WO 2015/178413 A1 | 11/2015 |
| WO | WO 2016/103002 A1 | 6/2016 |
| WO | WO 2016/115537 A2 | 7/2016 |
| WO | WO 2017/087032 A1 | 5/2017 |
| WO | WO 2017/178662 A1 | 10/2017 |

OTHER PUBLICATIONS

Fernandez et al., "TP53 mutations detected in circulating tumor cells present in the blood of metastatic triple negative breast cancer patients," Breast Cancer Research, vol. 16, No. 445, 2014, pp. 1-11.

Takai, "Bio-interface for Highly Sensitive Blood Analysis Chip," Surface Science, vol. 32 No. 9, 2011, pp. 575-580, with English abstract.

Nel et al., "Circulating tumor cell composition and outcome in patients with solid tumors," International Journal of Clinical Pharmacology and Therapeutics, vol. 52, No. 1, 2014, pp. 74-75, 2 pages total.

U.S. Office Action for U.S. Appl. No. 16/249,444, dated Apr. 26, 2022.

Gach et al., "Micropallet Arrays for the Capture, Isolation and Culture of Circulating Tumor Cetls From Whole Blood of Mice Engrafted With Primary Human Pancreatic Adenocarcinoma", Biosensors and Bioelectronics, vol. 54, 2014, (Available online Nov. 18, 2013), pp. 476-483.

Miltenyi Biotec, "Isolation of mononuclear cells from human peripheral blood by density gradient centrifugation," MACS, 2008, pp. 1-2.

Xu et al., "Optimization and Evaluation of a Novel Size Based Circulating Tumor Cell Isolation System," PLOS One, Sep. 23, 2015, pp. 1-23.

He et al, "Quantitation of Circulating Tumor Cells in Blood Samples from Ovarian and Prostate Cancer Patients Using Tumor-Specific Fluorescent Ligands", International Journal of Cancer, vol. 123, 2008, pp. 1968-1973.

Hoshiba et al., "Blood-compatible poly (2-methoxyethyl acrylate) for the adhesion and proliferation of lung cancer cells toward the isolation and analysis of circulating tumor cells," Journal of Bioactive and Compatible Polymers (2016), vol. 31, No. 4, pp. 361-372.

Hoshiba et al., "Adhesion-Based Simple Capture and Recovery of Circulating Tumor Cells Using a Blood-Compatible and Thermo-Responsive Polymer-Coated Substrate," RSC Advances, vol. 6, 2016 (Published on Sep. 13, 2016), pp. 89103-89112.

Khoo et al, "Liquid Biopsy and Therapeutic Response: Circulating Tumor Cell Cultures for Evaluation of Anticancer Treatment," Sci. Adv., vol. 2, e1600274, Jul. 13, 2016, pp. 1-15 (total 16 pages).

Khoo et al., Oncolarget, vol. 6, No. 17, May 6, 2015, pp. 15578-15593.

Klöckner et al., "Advances in shaking technologies," Trends in Biotechnology, vol. 30, No. 6, Jun. 2012, pp. 307-314.

Sansyo General Catalogue, "Tissue Culture and Filtration Ware, IWAKI Tissue Culture Ware," 2015 pp. 7 (total 2 pages).

Vona et al., "Isolation by Size of Epithelial Tumor Cells, a New Method for the Immunomorphological and Molecular Characterization of Circulating Tumor Cells," American Journal of Pathology, vol. 156, No. 1, Jan. 2000, pp. 57-63.

Williams, "Circulating Tumor Cells," PNAS, vol. 110, No. 13, Mar. 26, 2013, pp. 4861.

Yamamura et al., "Accurate Detection of Carcinoma Cells by Use of a Cell Microarray Chip," Plos One, vol. 7, Issue 3, Mar. 1, 2012, 832370 (9 pages total).

Yao et al., "Functional Analysis of Single Cells Identifies a Rare Subset of Circulating Tumor Cells with Malignant Traits," Integr Biol (Camb), vol. 6, No. 4, Apr. 2014, pp. 388-398 (total 20 pages).

Rosenberg et al.. "Comparison of Two Density Gradient Centrifugation Systems for the Enrichment of Disseminated Tumor Cells in Blood," Cytometry, vol. 49, 2002, pp. 150-158.

Vissers et al., "Rapid purification of human peripheral blood monocytes by centrifugation through Ficoll-Hypaque and Sepracell-MN," Journal of Immunological Methods, vol. 110, 1988, pp. 203-207.

* cited by examiner

A-A cross-sectional view

SPECIFIC CELL FRACTIONATING AND CAPTURING METHODS

TECHNICAL FIELD

The present invention relates to a method for fractionating (separating) specific cells in blood or biological fluid (e.g., cancer cells or stem cells present in blood or biological fluid), and a method for capturing the cells.

BACKGROUND ART

When cancer cells are formed, they are known to appear in due course in blood or biological fluid. Such cancer cells in blood are called "circulating tumor cells (CTCs)". Thus, it is expected that the circulating tumor cells may be analyzed, e.g., to evaluate the cancer-treating effect, predict prognosis life expectancy, predict the effect of anticancer drugs before administration, or examine treatment methods based on genetic analysis of cancer cells.

However, a problem exists in that since the number of circulating tumor cells is very small (several to hundreds of cells/1 mL of blood), such cancer cells are difficult to fractionate and capture.

For example, the CellSearch System is known as a technique for capturing circulating tumor cells. This technique, which involves an antigen-antibody reaction (capture by EpCAM antibody), can only capture cancer cells expressing EpCAM, and the type of cancer cells that can be captured is limited (see, for example, Patent Literature 1).

CITATION LIST

Patent Literature

Patent Literature 1: JP 2005-523981 T

SUMMARY OF INVENTION

Technical Problem

The present invention aims to solve the problem and provide specific cell-fractionating and -capturing methods which can fractionate and capture, respectively, specific cells (e.g., many types of cancer cells, including cancer cells not expressing EpCAM, or peripheral blood stem cells).

Solution to Problem

The present invention relates to a method for fractionating specific cells present in blood or biological fluid, the method including fractionating the blood or biological fluid by centrifugation to collect the specific cells in the blood or biological fluid, the centrifugation being carried out using a container having a low protein adsorbing layer at least partially formed on an inner surface thereof.

Preferably, the method for fractionating specific cells includes collecting a fraction layer and upper and lower layers respectively above and below the fraction layer formed by the fractionation by centrifugation, and the upper and lower layers to be collected each have a thickness that is not more than 2.0 times a thickness of the fraction layer.

Preferably, the method for fractionating specific cells includes collecting a fraction line or layer and upper and lower layers respectively above and below the fraction line or layer formed by the fractionation by centrifugation, and the upper and lower layers to be collected each have a thickness of 5.0 mm or less.

In the method for fractionating specific cells, a separation liquid is preferably used in the fractionation by centrifugation.

In the method for fractionating specific cells, the separation liquid preferably has a density of 1.060 to 1.115 g/mL.

In the method for fractionating specific cells, the separation liquid preferably has a density of 1.060 to 1.085 g/mL.

In the method for fractionating specific cells, the inner surface of the container preferably at least partially has a contact angle with water of 30 degrees or less.

Preferably, the method for fractionating specific cells includes mixing the blood or biological fluid with a hemolytic agent, followed by the centrifugation.

Preferably, the method for fractionating specific cells includes agglutinating blood cells in the blood or biological fluid, followed by the centrifugation.

The present invention also relates to a method for capturing specific cells present in blood or biological fluid, the method including fractionating the blood or biological fluid by centrifugation to collect the specific cells in the blood or biological fluid, and then capturing the specific cells present in the collected liquid onto a hydrophilic polymer layer, the centrifugation being carried out using a container having a low protein adsorbing layer at least partially formed on an inner surface thereof.

Preferably, the method for capturing specific cells includes collecting a fraction layer and upper and lower layers respectively above and below the fraction layer formed by the fractionation by centrifugation, and then capturing the specific cells present in the collected liquid onto a hydrophilic polymer layer, and the upper and lower layers to be collected each have a thickness that is not more than 2.0 times a thickness of the fraction layer.

Preferably, the method for capturing specific cells includes collecting a fraction line or layer and upper and lower layers respectively above and below the fraction line or layer formed by the fractionation by centrifugation, and then capturing the specific cells present in the collected liquid onto a hydrophilic polymer layer, and the upper and lower layers to be collected each have a thickness of 5.0 mm or less.

In the method for capturing specific cells, a separation liquid is preferably used in the fractionation by centrifugation.

In the method for capturing specific cells, the separation liquid preferably has a density of 1.060 to 1.115 g/mL.

In the method for capturing specific cells, the separation liquid preferably has a density of 1.060 to 1.085 g/mL.

In the method for capturing specific cells, the inner surface of the container preferably at least partially has a contact angle with water of 30 degrees or less.

Preferably, the method for capturing specific cells includes mixing the blood or biological fluid with a hemolytic agent, followed by the centrifugation.

Preferably, the method for capturing specific cells includes agglutinating blood cells in the blood or biological fluid, followed by the centrifugation.

Preferably, the method for capturing specific cells includes diluting the blood or biological fluid and then agglutinating blood cells in the blood or biological fluid, followed by the centrifugation.

Preferably, the method for capturing specific cells includes agglutinating blood cells in the blood or biological fluid and then diluting the blood or biological fluid, followed by the centrifugation.

In the method for capturing specific cells, the agglutinating blood cells preferably includes an antigen-antibody reaction.

In the method for capturing specific cells, the specific cells are preferably cancer cells.

In the method for capturing specific cells, the hydrophilic polymer layer is preferably formed of at least one hydrophilic polymer selected from the group consisting of poly(meth)acryloylmorpholine and polymers represented by the following formula (I):

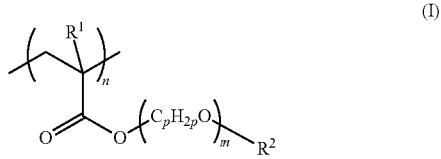

(I)

wherein $R^1$ represents a hydrogen atom or a methyl group; $R^2$ represents an alkyl group; p represents 1 to 8; m represents 1 to 5; and n represents the number of repetitions.

In the method for capturing specific cells, the hydrophilic polymer layer is preferably formed of a copolymer of at least one hydrophilic monomer selected from the group consisting of (meth)acryloylmorpholine and compounds represented by the following formula (II):

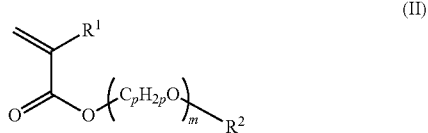

(II)

wherein $R^1$, $R^2$, p, and m are as defined above, with an additional monomer.

In the method for capturing specific cells, the hydrophilic polymer layer preferably has a thickness of 10 to 800 nm.

In the method for capturing specific cells, preferably fibronectin is adsorbed on a surface of the hydrophilic polymer layer.

Advantageous Effects of Invention

One aspect of the present invention relates to a method for fractionating specific cells present in blood or biological fluid. The method includes fractionating the blood or biological fluid by centrifugation to collect the specific cells in the blood or biological fluid. Further, the centrifugation is carried out using a container having a low protein adsorbing layer at least partially formed on the inner surface thereof. Such a method can effectively fractionate specific cells (e.g., many types of cancer cells, including cancer cells not expressing EpCAM). Thus, it is possible to sufficiently fractionate specific cells such as cancer cells from blood or biological fluid.

Another aspect of the present invention relates to a method for capturing specific cells present in blood or biological fluid. The method includes fractionating the blood or biological fluid by centrifugation to collect the specific cells in the blood or biological fluid, and then capturing the specific cells present in the collected liquid onto a hydrophilic polymer layer. Further, the centrifugation is carried out using a container having a low protein adsorbing layer at least partially formed on the inner surface thereof. Such a method can effectively capture specific cells (e.g., many types of cancer cells, including cancer cells not expressing EpCAM) and can also reduce adhesion or attachment of blood cells including red blood cells, white blood cells, and platelets. Thus, it is possible to selectively capture specific cells such as cancer cells from blood or biological fluid.

DESCRIPTION OF EMBODIMENTS

Figure 1A:
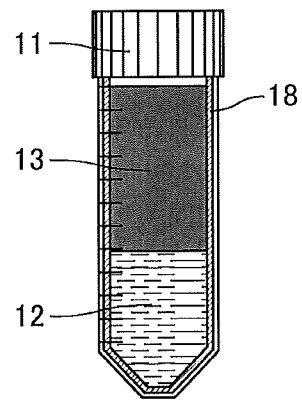
FIGS. 1A-1B illustrate exemplary schematic views of blood or biological fluid before and after being subjected to centrifugation.

The specific cell-fractionating method of the present invention is a method for fractionating specific cells present in blood or biological fluid. The method includes fractionating the blood or biological fluid by centrifugation to collect the specific cells in the blood or biological fluid. Further, the centrifugation is carried out using a container having a low protein adsorbing layer at least partially formed on the inner surface.

The specific cell-capturing method of the present invention is a method for capturing specific cells present in blood or biological fluid. The method includes fractionating the blood or biological fluid by centrifugation to collect the specific cells in the blood or biological fluid, and then capturing the specific cells present in the collected liquid onto a hydrophilic polymer layer. Further, the centrifugation is carried out using a container having a low protein adsorbing layer at least partially formed on the inner surface.

Specifically, according to the present methods, blood or biological fluid sampled from, e.g., the body may be first fractionated by centrifugation using a container having a low protein adsorbing layer at least partially formed on the inner surface, into a sample having blood cell levels lower than the sampled blood or biological fluid and enriched in specific cells such as cancer cells. Next, the prepared (fractionated) sample may be brought into contact with a hydrophilic polymer layer to capture the specific cells in the sample onto the polymer layer. This provides improved fractionation/separation of blood cells such as red blood cells and platelets, as well as reduced adsorption of specific cells such as cancer cells onto containers, resulting in a reduction in the loss of specific cells (e.g., the loss caused by the adsorption of specific cells onto containers used in fractionation/separation and enrichment processes). Thus, as the cell adhesion-inhibiting effect of blood cells and the like is reduced, specific cells exhibit their inherent ability to adhere to hydrophilic polymers. Therefore, the present methods provide greatly improved capture of specific cells such as cancer cells and reduced capture of blood cells, thereby achieving an effect of selectively capturing specific cells such as cancer cells. This effect could never be produced when a loss of specific cells occurs during the fractionation/separation and enrichment processes, and blood cells are present at high levels.

For example, first, sampled blood or biological fluid may be subjected to centrifugation using the specific container to fractionate/separate (remove) blood cells such as red blood cells, white blood cells, and platelets, and other components from the blood or biological fluid, thereby preparing a sample containing them at lower levels while reducing the loss of specific cells. Subsequently, the sample may be brought into contact with a hydrophilic polymer layer to selectively capture the specific cells. Thus, the specific cells such as cancer cells in the blood or biological fluid can be effectively captured onto the hydrophilic polymer layer. Then, it can be expected that by counting the number of captured cancer cells or the like, one can determine the number of cancer cells or the like in the blood or biological fluid, e.g., in order to evaluate the cancer-treating effect. Moreover, the captured cancer cells or the like may be cultured and then used to determine the effect of drugs such as anticancer drugs. This allows one to determine the effect of drugs such as anticancer drugs ex vivo before administration, and also helps to screen drugs such as anticancer drugs. Furthermore, the captured cancer cells or the like may be cultured and then used for various analyses (gene analysis, pathologic analysis, etc.) of cancer cells or the like.

The specific cell-fractionating and -capturing methods are a method for fractionating specific cells present in blood or biological fluid and a method for capturing the fractionated specific cells, respectively. Examples of the specific cells include cancer cells (any cancer cells, including cancer cells not expressing EpCAM, and peripheral blood stem cells). Examples of the cancer cells include circulating tumor cells (CTCs).

In the specific cell-fractionating and -capturing methods, blood or biological fluid is centrifuged using a container having a low protein adsorbing layer at least partially formed on the inner surface to fractionate specific cells.

The low protein adsorbing layer may be any layer having low protein adsorbing properties, such as layers formed of low protein adsorbing polymers. Specific suitable examples include low protein adsorbing layers formed of low protein adsorbing polymers produced by polymerizing low protein adsorbing monomers, such as alkali metal-containing monomers (monomers containing alkali metals in the molecule) and zwitterionic monomers (zwitterionic group-containing compounds: compounds bearing a center of permanent positive charge and a center of negative charge). These monomers may be used alone or in combinations of two or more. It should be noted that monomers corresponding both to alkali metal-containing monomers and to zwitterionic monomers are included in both monomer types.

Examples of the alkali metal-containing monomers include alkali metal salts of acrylic acid such as sodium acrylate and potassium acrylate; alkali metal salts of methacrylic acid such as sodium methacrylate and potassium methacrylate; alkali metal salts of itaconic acid such as sodium itaconate and potassium itaconate; alkali metal salts of 3-vinylpropionic acid such as sodium 3-vinylpropionate and potassium 3-vinylpropionate; alkali metal salts of vinylsulfonic acid such as sodium vinylsulfonate and potassium vinylsulfonate; alkali metal salts of 2-sulfoethyl (meth)acrylate such as sodium 2-sulfoethyl (meth)acrylate and potassium 2-sulfoethyl (meth)acrylate; alkali metal salts of 3-sulfopropyl (meth)acrylate such as sodium 3-sulfopropyl (meth)acrylate and potassium 3-sulfopropyl (meth)acrylate; alkali metal salts of 2-acrylamide-2-methylpropanesulfonic acid such as sodium 2-acrylamide-2-methylpropanesulfonate and potassium 2-acrylamide-2-methylpropanesulfonate; and alkali metal salts of styrenesulfonic acid such as sodium styrenesulfonate and potassium styrenesulfonate. Preferred among these is potassium 3-sulfopropyl methacrylate.

Examples of the zwitterionic monomers include carboxybetaines, sulfobetaines, and phosphobetaines, and also include compounds represented by the following formula (1), among which compounds represented by the formula (2) below are suitable.

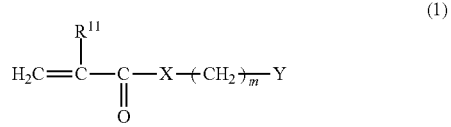

(1)

In the formula, $R^{11}$ represents —H or —CH$_3$; X represents —O—, —NH—, or —NH—, —N$^+$—; m represents an integer of 1 or larger; and Y represents a zwitterionic group or a halogen group such as Cl$^-$, Br$^-$, or F$^-$.

In formula (1), preferably, $R^{11}$ is —CH$_3$, X is —O—, and m is an integer of 1 to 10. In the zwitterionic group designated by Y, the cation may be a quaternary ammonium such as tetraalkylammonium, and the anion may be a carboxylate, sulfonate, or phosphate.

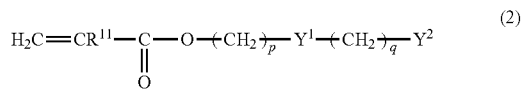

(2)

In the formula, $R^{11}$ represents —H or —CH$_3$; p and q each represent an integer of 1 or larger; and $Y^1$ and $Y^2$ represent ionic functional groups having electric charges opposite to each other.

In formula (2), p is preferably an integer of 2 or larger, more preferably an integer of 2 to 10, and q is preferably an integer of 1 to 10, more preferably an integer of 2 to 4. $R^{11}$ is preferably as described above. $Y^1$ and $Y^2$ are as described for the cation and anion above.

Typical suitable examples of the zwitterionic monomers include compounds represented by the following formulas (2-1) to (2-4):

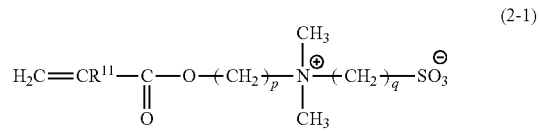

(2-1)

wherein $R^{11}$ represents a hydrogen atom or a methyl group, and p and q each represent an integer of 1 to 10,

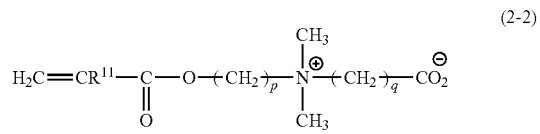

(2-2)

wherein $R^{11}$ represents a hydrogen atom or a methyl group, and p and q each represent an integer of 1 to 10,

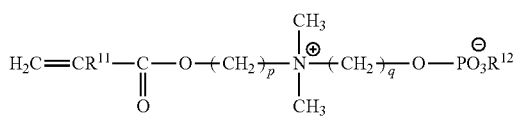

(2-3)

wherein $R^{11}$ represents a hydrogen atom or a methyl group; $R^{12}$ represents a C1-C6 hydrocarbon group; and p and q each represent an integer of 1 to 10, and

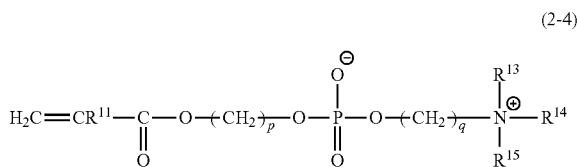

(2-4)

wherein $R^{11}$ represents a hydrogen atom or a methyl group; $R^{13}$, $R^{14}$, and $R^{15}$ are the same as or different from one another and each represent a C1 or C2 hydrocarbon group; and p and q each represent an integer of 1 to 10.

Examples of compounds represented by formula (2-1) include dimethyl(3-sulfopropyl) (2-(meth)acryloyloxyethyl)-ammonium betaine. Examples of compounds represented by formula (2-2) include dimethyl(2-carboxyethyl) (2-(meth)acryloyloxyethyl)ammonium betaine. Examples of compounds represented by formula (2-3) include dimethyl(3-methoxyphosphopropyl) (2-(meth)acryloyloxyethyl)ammonium betaine. Examples of compounds represented by formula (2-4) include 2-(meth)acryloyloxyethyl phosphorylcholine. Other examples of the zwitterionic monomers include 2-(meth)acryloyloxyethyl carboxybetaine and 2-(meth)acryloyloxyethyl sulfobetaine. Among these, 2-(meth)acryloyloxyethyl phosphorylcholine (MPC) is preferred because of its high biocompatibility and low protein adsorbing properties.

From the standpoint of low protein adsorbing properties, the low protein adsorbing polymer preferably has a number average molecular weight (Mn) of 10,000 to 200,000, more preferably 10,000 to 150,000. The Mn herein can be determined by gel permeation chromatography (GPC) (GPC-8000 series produced by TOSOH Corporation, detector: differential refractometer, column: TSKGEL SUPERMULTIPORE HZ-M produced by TOSOH Corporation) calibrated with polystyrene standards.

The container used in the centrifugation has a low protein adsorbing layer at least partially formed on the inner surface. The low protein adsorbing layer preferably has a thickness of 20 to 10,000 nm, more preferably 50 to 800 nm, still more preferably 50 to 500 nm. When the thickness is adjusted within the range indicated above, low adsorption of proteins can be well achieved. The low protein adsorbing layer is preferably formed over a large area on the inner surface. Suitably, the low protein adsorbing layer is formed on the entire inner surface.

The low protein adsorbing layer may be formed from a low protein adsorbing polymer by dissolving or dispersing the low protein adsorbing polymer in any solvent to prepare a low protein adsorbing polymer solution or dispersion, and entirely or partially coating the inner surface of the container with the low protein adsorbing polymer solution or dispersion by a known method, such as 1) by injecting the low protein adsorbing polymer solution or dispersion into the container and holding and drying it for a predetermined time, or 2) by applying (spraying) the low protein adsorbing polymer solution or dispersion to the inner surface of the container and holding and drying it for a predetermined time.

The solvent, injection method, application (spraying) method, and other conditions may be conventionally known materials or methods.

The holding and drying times in the method 1) or 2) may be selected appropriately according to the size of the container, the type of liquid introduced, and other factors. The holding and drying temperatures may be appropriately selected.

The solvent may be any solvent that can dissolve the low protein adsorbing polymer and may be selected appropriately depending on the low protein adsorbing polymer used. Examples include water, organic solvents, and solvent mixtures thereof. Examples of the organic solvents include alcohols such as methanol, ethanol, n-propanol, i-propanol, and methoxypropanol, ketones such as acetone and methyl ethyl ketone, tetrahydrofuran, acetonitrile, ethyl acetate, and toluene.

From the standpoint of collecting specific cells, the inner surface of the container used in the centrifugation (the container having a low protein adsorbing layer at least partially formed on the inner surface) preferably at least partially has a contact angle with water of 30 degrees or less, more preferably 20 degrees or less, still more preferably 10 degrees or less.

The contact angle with water may be measured by dropping 2 μL of distilled water onto the inner surface of the container and 30 seconds later measuring the contact angle by the θ/2 method (at room temperature).

The centrifugation may be carried out by known methods, for example, using known centrifugal separators.

The centrifugation is preferably carried out at a centrifugal force of 200 to 3,000 G (×G). A centrifugal force of 200 G or higher provides improved separation of blood cells and reduction in the loss of specific cells (the loss due to the specific cells being incorporated into the fraction of red blood cells and the like), thereby being effective in selectively capturing specific cells. A centrifugal force of 3000 G or lower can result in reduced stress on specific cells, thereby maintaining their original nature. The centrifugal force is more preferably 300 to 2,800 G, still more preferably 400 to 2,500 G.

The duration and temperature of the centrifugation may be appropriately selected, e.g., from the standpoint of separating blood cells. For example, the centrifugation may be performed for 1 to 120 minutes, preferably 1 to 60 minutes, at 2 to 40° C., preferably 3 to 30° C.

In the centrifugation, preferably a separation liquid is used in the fractionation by centrifugation. This enables suitable fractionation into a mononuclear cell layer containing specific cells (e.g., cancer cells), a layer containing red blood cells and the like, and other layers.

The separation liquid to be used in density-gradient centrifugation may be prepared such that it has a specific gravity suited for fractionating cells in blood and also has an osmotic pressure and pH that do not destroy cells. The medium used may be one that is usable in density-gradient centrifugation. The separation liquid preferably has a specific gravity at 20° C. of 1.060 to 1.115 g/mL. The separation liquid preferably has a pH of 4.5 to 7.5.

Typical examples of the medium (separation liquid) include sucrose, ficoll (a copolymer of sucrose and epichlorohydrin), and percoll (polyvinylpyrrolidone-coated colloidal silica product). Examples of commercial products of ficoll include Ficoll-Paque PLUS (Pharmacia Biotech), Histopaque-1077 (Sigma-Aldrich Japan), and Lymphoprep (Nycomed, Oslo, Norway). Examples of commercial products of percoll include Percoll (Sigma-Aldrich Japan).

From the standpoint of collecting specific cells, the separation liquid preferably has a density (20° C.) of 1.060 to 1.115 g/mL, more preferably 1.060 to 1.085 g/mL.

Suitable embodiments of the specific cell-fractionating method includes 1) a method including collecting a fraction layer and upper and lower layers respectively above and below the fraction layer formed by the fractionation by centrifugation, wherein the upper and lower layers to be collected each have a thickness that is not more than 2.0 times the thickness of the fraction layer; and 2) a method including collecting a fraction line or layer and upper and lower layers respectively above and below the fraction line or layer formed by the fractionation by centrifugation, wherein the upper and lower layers to be collected each have a thickness of 5.0 mm or less.

Suitable embodiments of the specific cell-capturing method include (3) a method including collecting a fraction layer and upper and lower layers respectively above and below the fraction layer formed by the fractionation by centrifugation, and then capturing the specific cells present in the collected liquid onto a hydrophilic polymer layer, wherein the upper and lower layers to be collected each have a thickness that is not more than 2.0 times the thickness of the fraction layer; and (4) a method including collecting a fraction line or layer and upper and lower layers respectively above and below the fraction line or layer formed by the fractionation by centrifugation, and then capturing the specific cells present in the collected liquid onto a hydrophilic polymer layer, wherein the upper and lower layers to be collected each have a thickness of 5.0 mm or less.

Figure 1B:
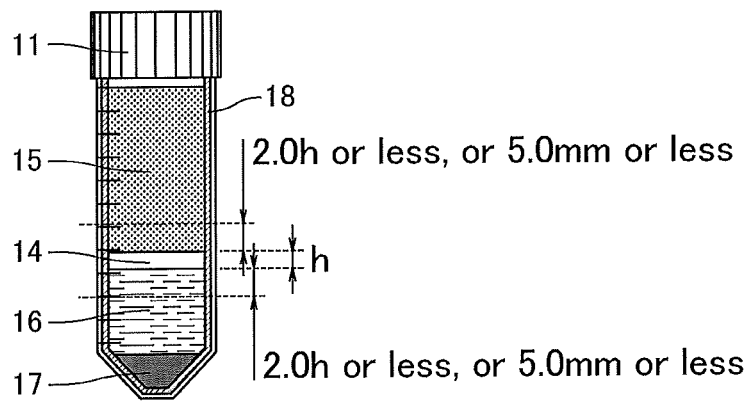

FIG. 1 illustrate exemplary schematic views of blood or biological fluid before and after being subjected to centrifugation. FIG. 1A illustrates an exemplary schematic view before centrifugation, in which a separation liquid 12 and a sample (blood or biological fluid, or a dilution thereof) 13 are placed in a centrifugal container (centrifuge tube) 11 having a low protein adsorbing layer 18 formed on the inner surface, while FIG. 1B illustrates an exemplary schematic view of FIG. 1A after being subjected to centrifugation. FIG. 1B illustrates that a fraction layer or line 14 containing specific cells (mononuclear cell layer), an upper layer 15 (also referred to as "supernatant (platelet-containing supernatant)") above the fraction layer or line 14, a lower layer 16 (also referred to as "subnatant (separation liquid-containing subnatant)") below the faction layer or line 14, and a red blood cell-containing layer 17 below the lower layer 16 are fractionated in the centrifugal container (centrifuge tube) 11 having the low protein adsorbing layer 18 formed on the inner surface.

In the embodiments (1) and (3), after the fractionation by centrifugation as illustrated in FIG. 1B, the specific cell-containing fraction layer 14 (mononuclear cell layer), a portion of the upper layer 15 (supernatant) having a thickness from the interface with the fraction layer 14 toward the upper layer (toward the upper side in FIG. 1B) that is at most 2.0 times the thickness h of the fraction layer 14 (a thickness of 2.0×h or less), and a portion of the lower layer 16 (subnatant) having a thickness from the interface with the fraction layer 14 toward the lower side in FIG. 1B) that is at most 2.0 times the thickness h of the fraction layer 14 (a thickness of 2.0×h or less) are collected.

In the embodiments (2) and (4), after the fractionation by centrifugation as illustrated in FIG. 1B, the specific cell-containing fraction layer or line 14 (mononuclear cell layer), a portion of the upper layer 15 (supernatant) having a thickness from the interface with the fraction layer or line 14 toward the upper layer (toward the upper side in FIG. 1B) of at most 5.0 mm (a thickness of 5.0 mm or less), and a portion of the lower layer 16 (subnatant) having a thickness from the interface with the fraction layer or line 14 toward the lower layer (toward the lower side in FIG. 1B) of at most 5.0 mm (a thickness of 5.0 mm or less) are collected.

Through the fractionation by centrifugation and collection as described above, even specific cells which are not completely fractionated by centrifugation can be collected from the predetermined portions of the upper and lower layers above and below the mononuclear cell layer, and therefore the specific cells can be collected without loss. It is thus possible to prepare samples from which red blood cells and platelets have been separated and removed and which contain higher levels of specific cells such as cancer cells.

In the embodiments (1) and (3), the thickness of the upper layer (supernatant) or lower layer (subnatant) to be collected is not more than 2.0 times the thickness of the fraction layer. From the standpoint of capturing specific cells, it is preferably not more than 1.5 times, more preferably not more than 1.2 times the thickness of the fraction layer. From the standpoint of collecting specific cells, the lower limit is preferably not less than 0.1 times, more preferably not less than 0.3 times the thickness of the fraction layer.

In the embodiments (2) and (4), the thickness of the upper layer (platelet-containing supernatant) or lower layer (separation liquid-containing subnatant) to be collected is 5.0 mm or less. From the standpoint of capturing specific cells, it is preferably 3.0 mm or less, more preferably 2.0 mm or less. From the standpoint of collecting specific cells, the lower limit is preferably 0.5 mm or more, more preferably 1.0 mm or more.

To further reduce red blood cells in the fractions to be collected, the specific cell-fractionating method preferably includes mixing (adding) a hemolytic agent with (to) the blood or biological fluid, followed by the centrifugation. Hemolytic agents physically or chemically act on red blood cells to lyse the red blood cells. The hemolytic agent may be a conventional one. Examples include ammonium chloride, synthetic surfactants, and alcohols.

The specific cell-fractionating method preferably includes agglutinating blood cells in the blood or biological fluid, followed by the centrifugation. In other words, the centrifugation is preferably preceded by agglutinating blood cells in the blood or biological fluid. Blood cells may be agglutinated by any method that can cause such agglutination. Among such methods, those based on antigen-antibody reactions are suitable. Specifically, methods based on agglutination reactions such as hemagglutination may be suitably used.

When the blood cells in the blood or biological fluid are agglutinated via hemagglutination to prepare a sample containing agglutinates in the agglutination step, the agglutinates including blood cells can be removed by the subsequent centrifugation of the sample. Thus, the high levels of specific cells (e.g., cancer cells) remaining in the sample can be effectively captured onto the hydrophilic polymer layer.

The agglutination of blood cells may be suitably carried out using, for example, an antibody reagent for agglutinating red and white blood cells (an antibody composition for agglutinating red and white blood cells). In spite of the fact that some white blood cells having specific gravities close to the specific cells such as cancer cells can be poorly separated by centrifugation, when red and white blood cells are bound and agglutinated via an antigen-antibody reaction using the antibody composition, the specific cells can be well separated not only from red blood cells, platelets, and the like having specific gravities different from the specific cells, but also from white blood cells. Thus, it is possible to improve adhesion and capture of the specific cells.

The blood or biological fluid may be diluted before the agglutination of blood cells, followed by the centrifugation. The dilution may be performed using a buffer solution such as a phosphate buffered saline (PBS) having the same pH as human blood (about 7.4) or a liquid medium such as Dulbecco's modified eagle's medium (DMEM). Specifically, it may be carried out by diluting the sampled blood or biological fluid with a buffer solution, or adding the sampled blood or biological fluid to a liquid medium for dilution. The dilution process provides protein levels lower than the sampled blood or biological fluid.

Alternatively, after the agglutination of blood cells, the blood or biological fluid may be diluted, followed by the centrifugation. The dilution process may be performed as described above.

In the specific cell-capturing method, the specific cells present in the collected liquid (fractionated liquid) fractionated by the above-described specific cell-fractionating method are captured onto a hydrophilic polymer layer.

The hydrophilic polymer layer (the layer formed of a hydrophilic polymer) may be formed on a certain substrate.

Examples of the substrate include acrylic resins (polyacrylic resins) such as polymethyl acrylate, polymethyl methacrylate, polyacrylic acid, and polymethacrylic acid; cycloolefin resins (polycycloolefins); carbonate resins (polycarbonates); styrene resins (polystyrenes); polyester resins such as polyethylene terephthalate (PET); polydimethylsiloxanes; and glass such as soda-lime glass and borosilicate glass. Preferred among these are polyacrylic resins and soda-lime glass because it is preferred to use a substrate made of a more hydrophilic material for coating with the hydrophilic polymer.

The hydrophilic polymer layer (the layer formed of a hydrophilic polymer) preferably has a thickness of 10 to 800 nm, more preferably 30 to 550 nm, still more preferably 50 to 400 nm. When the thickness is adjusted within the range indicated above, selective capture of cancer cells and low adsorption of other proteins and cells can be well achieved.

The hydrophilic polymer may be appropriately selected from polymers having hydrophilicity. For example, it may be a homopolymer or copolymer of one or two or more hydrophilic monomers, or a copolymer of one or two or more hydrophilic monomers with an additional monomer. Examples of the homopolymer or copolymer include polyacrylic acid, polyacrylic acid esters, polymethacrylic acid, polymethacrylic acid esters, polyacryloylmorpholine, polymethacryloylmorpholine, polyacrylamide, and polymethacrylamide.

The hydrophilic monomer(s) used in the homopolymer or copolymer may be any monomer containing a hydrophilic group. Examples of the hydrophilic group include known hydrophilic groups such as an amide group, a sulfuric acid group, a sulfonic acid group, a carboxylic acid group, a hydroxyl group, an amino group, and an oxyethylene group.

Specific examples of the hydrophilic monomers include (meth)acrylic acid, (meth)acrylic acid esters (e.g., alkoxyalkyl (meth)acrylates such as methoxyethyl (meth)acrylate, and hydroxyalkyl (meth)acrylates such as hydroxyethyl (meth)acrylate), (meth)acrylamide, and (meth)acrylamide derivatives having cyclic groups (e.g., (meth)acryloylmorpholine). Preferred among these are (meth)acrylic acid, (meth)acrylic acid esters, alkoxyalkyl (meth)acrylates, and (meth)acryloylmorpholine, with alkoxyalkyl (meth)acrylates being more preferred, with 2-methoxyethyl acrylate being particularly preferred.

The additional monomer used in the copolymer may be appropriately selected as long as it does not inhibit the effect of the hydrophilic polymer. Examples include aromatic monomers such as styrene, vinyl acetate, and N-isopropylacrylamide which can impart temperature responsiveness.

In particular, the hydrophilic polymer is preferably at least one selected from the group consisting of poly(meth)acryloylmorpholine and polymers represented by the following formula (I):

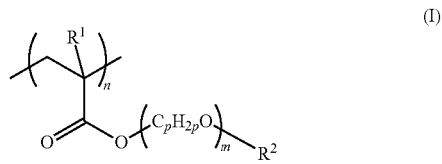

wherein $R^1$ represents a hydrogen atom or a methyl group; $R^2$ represents an alkyl group; p represents 1 to 8; m represents 1 to 5; and n represents the number of repetitions.

Suitable examples of the polymers of formula (I) include polymers represented by the following formula (I-1):

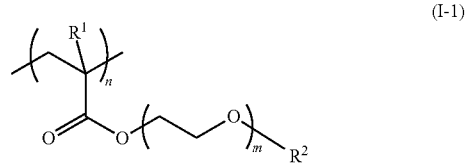

wherein $R^1$ represents a hydrogen atom or a methyl group; $R^2$ represents an alkyl group; m represents 1 to 5; and n represents the number of repetitions.

The carbon number of the alkyl group for $R^2$ is preferably 1 to 10, more preferably 1 to 5. In particular, $R^2$ is particularly preferably a methyl group or an ethyl group. The symbol p is preferably 1 to 5, more preferably 1 to 3; m is preferably 1 to 3; and n representing the number of repetitions is preferably 15 to 1500, more preferably 40 to 1200.

The hydrophilic polymer may suitably be a copolymer of at least one hydrophilic monomer selected from the group consisting of (meth)acryloylmorpholine and compounds represented by the following formula (II):

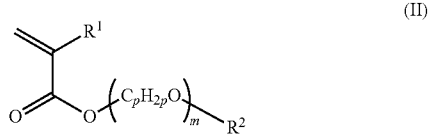

wherein $R^1$, $R^2$, p, and m are as defined above, with an additional monomer.

Suitable examples of the compounds of formula (II) include compounds represented by the following formula (II-1):

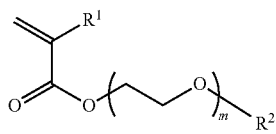

(II-1)

wherein R¹, R², and m are as defined above.

From the standpoint of selective adsorption or adhesion of cancer cells, the hydrophilic polymer preferably has a number average molecular weight (Mn) of 8,000 to 150,000, more preferably 10,000 to 60,000, still more preferably 12,000 to 50,000. The Mn herein can be determined by gel permeation chromatography (GPC) (GPC-8000 series produced by TOSOH Corporation, detector: differential refractometer, column: TSKGEL SUPERMULTIPORE HZ-M produced by TOSOH Corporation) calibrated with polystyrene standards.

The surface of the hydrophilic polymer layer preferably at least partially (partially or entirely) has a contact angle with water of 30 to 75 degrees, more preferably 35 to 75 degrees, still more preferably 35 to 70 degrees. When the hydrophilic polymer layer has such a predetermined contact angle with water, the advantageous effects can be well achieved.

The hydrophilic polymer layer may be formed by dissolving or dispersing a hydrophilic polymer in any solvent to prepare a hydrophilic polymer solution or dispersion, and entirely or partially coating the surface of a substrate with the hydrophilic polymer solution or dispersion by a known method, such as (1) by injecting the hydrophilic polymer solution or dispersion into the substrate surface (the recess of the substrate) and holding and drying it for a predetermined time, or (2) by applying (spraying) the hydrophilic polymer solution or dispersion to the substrate surface and holding and drying it for a predetermined time. Thus, a substrate provided with a polymer layer formed of a hydrophilic polymer can be prepared. Then, the substrate provided with a hydrophilic polymer layer may be combined with other components as needed, to prepare an apparatus capable of capturing specific cells.

The solvent, injection method, application (spraying) method, and other conditions may be conventionally known materials or methods.

The holding and drying times in the method 1) or 2) may be selected appropriately according to the size of the substrate, the type of liquid introduced, and other factors. The holding time is preferably five minutes to ten hours, more preferably ten minutes to five hours, still more preferably 15 minutes to two hours. The drying is preferably performed at room temperature (about 23° C.) to 80° C., more preferably at room temperature to 50° C. Moreover, the drying may be carried out under reduced pressure. Furthermore, the hydrophilic polymer solution or dispersion may be held for a certain period of time, optionally followed by discharging the excess solution or dispersion before drying.

The solvent may be any solvent that can dissolve the hydrophilic polymer and may be selected appropriately depending on the hydrophilic polymer used. Examples include water, organic solvents, and solvent mixtures thereof. Examples of the organic solvents include alcohols such as methanol, ethanol, n-propanol, i-propanol, and methoxypropanol, ketones such as acetone and methyl ethyl ketone, tetrahydrofuran, acetonitrile, ethyl acetate, and toluene.

Preferably, fibronectin is adsorbed on the surface of the hydrophilic polymer layer.

When the hydrophilic polymer layer on which fibronectin is adsorbed is brought into contact with the collected liquid (fractionated liquid), a larger amount of specific cells such as cancer cells can be adsorbed or attached onto the hydrophilic polymer layer.

Fibronectin may be adsorbed onto the hydrophilic polymer layer by any known method, such as by bringing the hydrophilic polymer layer into contact with a buffer solution (e.g., phosphate buffered saline (PBS)) containing fibronectin by a known method, and leaving them at a predetermined temperature for a predetermined time, optionally followed by washing. The temperature and time may be selected as appropriate, and may be, for example, about 10 to 60° C. and about 0.1 to 24 hours, respectively.

From the standpoint of adsorbing fibronectin onto the hydrophilic polymer layer, it is suitable to use a solution, dispersion, or other mixture adjusted to have a fibronectin concentration of preferably 0.5 to 500 µg/mL, more preferably 1 to 250 µg/mL. When the concentration is adjusted within the range indicated above, excellent capture of specific cells such as cancer cells can be achieved.

In the specific cell-capturing method, a sample (the collected liquid: a sample with lower blood cell levels) prepared by fractionating blood or biological fluid by centrifugation may be brought into contact with a substrate provided with a hydrophilic polymer layer to capture the specific cells in the sample. The contact between the sample and the hydrophilic polymer layer may be carried out by any method capable of this contact, such as by injecting or applying (spraying) the sample.

By contacting the sample with the hydrophilic polymer layer, the specific cells present in the sample can be captured onto the hydrophilic polymer layer while reducing adsorption of blood cells and the like. Thus, the specific cells may be selectively captured onto the hydrophilic polymer layer, for example, by holding the contacted sample for a predetermined time and then washing it. Then, it is expected that by counting the number of captured specific cells, one can determine the number of specific cells in the sampled blood or biological fluid, e.g., in order to evaluate the cancer-treating effect.

The specific cell-capturing method may be performed using, for example, a device that includes a substrate such as a single well (dish), a multi-well plate, or a chamber slide, optionally with additional components. FIG. 2 illustrate an exemplary multi-well plate 2.

Figure 2A:
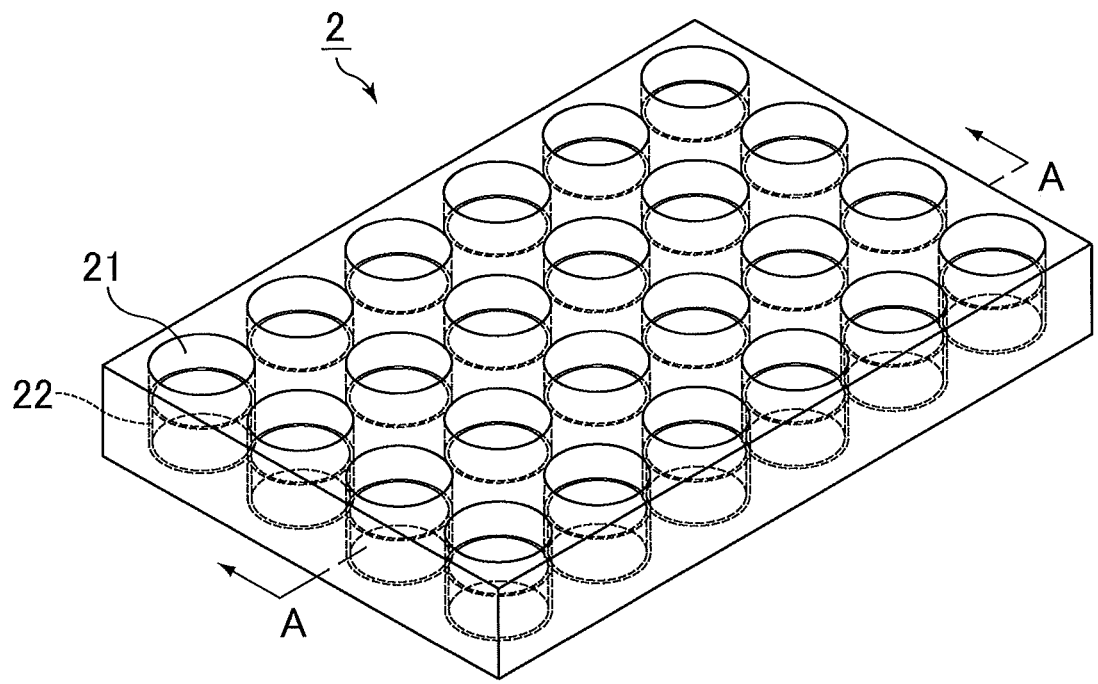
FIGS. 2A-2B illustrate exemplary schematic views of a multi-well plate with wells on which a hydrophilic polymer layer is formed.
Figure 2B:
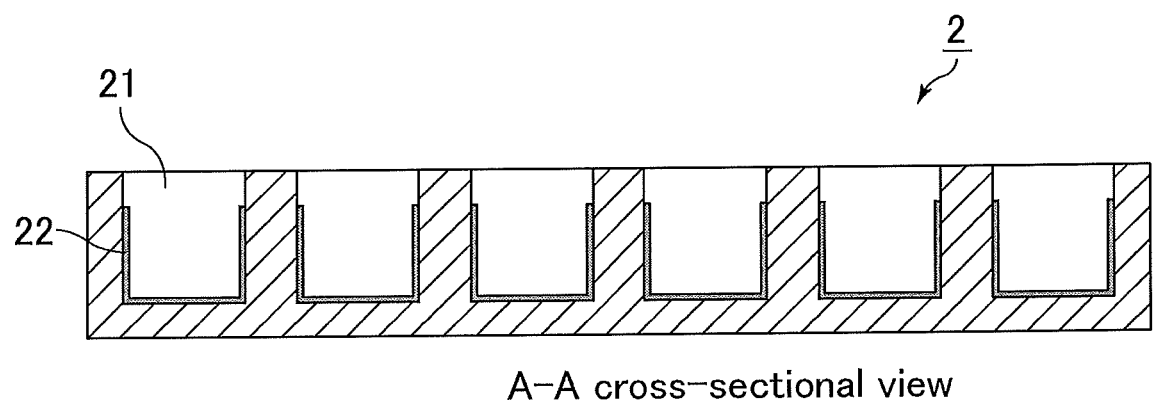

The multi-well plate 2 in FIGS. 2A and 2B is a device intended to capture specific cells, in which wells 21 are arranged in what is called matrix form. The multi-well plate 2 has multiple wells 21 having a circular opening. The wells 21 are recesses into which may be injected a sample prepared by fractionating sampled blood or biological fluid by centrifugation to reduce the levels of red blood cells, white blood cells, platelets, and the like. When the injected sample is subjected to analysis, specific cells can be effectively captured as compared to when the sampled blood or biological fluid is directly subjected to analysis. Thus, it is possible to confirm the presence or absence of specific cells in the blood or biological fluid, count the number of specific cells, culture the specific cells, determine the effect of drugs, and screen the drugs.

Although FIG. 2 illustrate an example of a 24-well plate having 24 wells 21 arranged in 4 rows by 6 columns, it is sufficient for the multi-well plate 2 to have at least two wells 21, and any number of wells 21 may be provided. Examples other than the 24-well plate include general multi-well plates in which the number of wells 21 is 6, 96, 384, etc.

Each well 21 is a blind hole which is opened at the surface of the multi-well plate 2. A sample prepared by fractionating blood or biological fluid by centrifugation may be injected into the wells 21 through the respective openings. If the presence of specific cells is confirmed, a culture fluid for culturing the specific cells may also be injected.

The diameter R of the opening and the depth D of each well 21 are not limited, and may be those of a conventional multi-well plate 2. Although in FIG. 2, the inner side surface of each well 21 is substantially vertical to the opposite faces of the multi-well plate 2, the inner side surface of each well 21 may be inclined to taper from the opening to the bottom. Alternatively, the inner side surface may be inclined to flare out from the opening to the bottom.

Though the wells 21 in FIG. 2 are circularly opened, the openings of the wells 21 may be of any shape such as quadrangle.

The multi-well plate 2 may be one in which the multiple wells 21 are separable. Since multiple wells are provided, they can be separated into wells for counting the number of specific cells and for culturing the specific cells. For example, the presence or absence of specific cells may first be confirmed in the counting wells, and if the presence is confirmed, the specific cells may be cultured in the culturing wells and then used to determine the effect of drugs. In a suitable chamber slide, the number of chambers is at least one but not more than ten.

In the single well (dish), multi-well plate 2, or chamber slide, the well(s) 21 or chamber(s) preferably have a hydrophilic polymer layer at least partially formed on the inner surface. In the example shown in FIG. 2B, a hydrophilic polymer layer 22 is formed on the bottom surface and a part of the side surface of the wells.

For use in cell observation, the wells or chambers are preferably made of a highly transparent material. Examples of such materials include those mentioned for the substrate.

Once a sample (the collected liquid or a suspension of the collected materials in, for example, a liquid medium) prepared by fractionating blood or biological fluid by centrifugation is introduced into the wells 21 provided with the hydrophilic polymer layer 22, the specific cells present in the sample can be captured onto the hydrophilic polymer layer 22 while reducing adsorption of blood cells and the like. Thus, the specific cells may be selectively captured onto the hydrophilic polymer layer 22 by holding the introduced sample for a predetermined time and then washing it.

The specific cell-capturing method enables capture of specific cells (e.g., many types of cancer cells, including cancer cells not expressing EpCAM). Moreover, this method can sufficiently capture specific cells from blood or biological fluid while reducing adhesion or attachment of other proteins and cells, thereby selectively capturing the specific cells.

In the specific cell-capturing method, the hydrophilic polymer layer may suitably be brought into contact with a sample (the collected liquid or a suspension of the collected materials in, for example, a liquid medium) from which blood cells and the like have been previously removed. This can further enhance selective capture of specific cells such as cancer cells. The removal of blood cells and the like may be carried out by the above-described centrifugation process as well as known techniques such as membrane separation.

EXAMPLES

The present invention is specifically described with reference to, but not limited to, examples below.

Specific cell-fractionating and -capturing methods were performed as described below. The results of Example a and Comparative Example a (specific cell-fractionating methods) are shown in Table 1; the results of Examples A to C and Comparative Example A (specific cell-capturing methods) are shown in Table 2; and the results of Examples 1 to 4 and Comparative Examples 1-1 to 1-3 and 2 to 5 (specific cell-fractionating or -capturing methods) are shown in Table 3.

Specific Cell-Fractionating Method

Example A

Stained human colon adenocarcinoma (HT-29) cells were suspended in whole blood at a concentration of 500,000 cells per mL of blood to prepare spiked blood. The spiked blood was diluted with an equal volume of a phosphate buffer solution to prepare a spiked blood dilution. Next, a separation liquid (Lymphoprep, density=1.077±0.001 g/mL) was placed in a 15 mL centrifuge tube coated with a copolymer of MPC and butyl methacrylate (poly MPC: a polymer that hardly adsorbs proteins). Then, the spiked blood dilution was placed on the liquid, followed by centrifugation at 800 G for 20 minutes at room temperature (about 23° C.). Then, a mononuclear cell layer (fraction layer, fraction line) was fractionated (collected). The inner surface of the pipette tips to be used to weigh, discharge, or inject the blood or solutions was coated with the poly MPC (a polymer that hardly adsorbs proteins). Then, the number of HT-29 cells in the fractionated (collected) solution was counted with a hemocytometer. The ratio of the number of cells in the collected solution to the initial number of cells was calculated to determine the cell recovery ratio (%).

Comparative Example A

The cell recovery ratio (%) was determined as in Example a, except that the centrifuge tube and pipette tips not coated with the poly MPC were used in the fractionation.

Example 1

Stained human colon adenocarcinoma (HT-29) cells were suspended in whole blood at a concentration of 10,000 cells per mL of blood to prepare spiked blood. The spiked blood was diluted with an equal volume of a phosphate buffer solution to prepare a spiked blood dilution. Next, a separation liquid (Lymphoprep, density=1.077±0.001 g/mL) was placed in a 15 mL centrifuge tube coated with a copolymer of MPC and butyl methacrylate (poly MPC: a polymer that hardly adsorbs proteins). Then, the spiked blood dilution was placed on the liquid, followed by centrifugation at 800 G for 20 minutes at room temperature (about 23° C.). Then, a mononuclear cell layer (fraction layer or line), a supernatant (upper layer) directly above the mononuclear cell layer having a thickness 2.0 times the thickness of the mononuclear cell layer, and a subnatant (lower layer) directly below the mononuclear cell layer having a thickness 2.0 times the thickness of the mononuclear cell layer were fractionated (collected). The inner surface of the pipette tips to be used to weigh, discharge, or inject the blood or solutions was coated with the poly MPC (a polymer that hardly adsorbs proteins). Then, the number of HT-29 cells in the fractionated (collected) solution was counted with a hemocytometer.

The ratio of the number of cells in the collected solution to the initial number of cells was calculated to determine the cell recovery ratio (%).

Comparative Example 1-1

The cell recovery ratio (%) was determined as in Example 1, except that the centrifuge tube and pipette tips not coated with the poly MPC were used in the fractionation.

Comparative Example 1-2

The cell recovery ratio (%) was determined as in Comparative Example 1-1, except that only the mononuclear cell layer was fractionated.

Comparative Example 1-3

The cell recovery ratio (%) was determined as in Comparative Example 1-1, except that the mononuclear cell layer, a supernatant directly above the mononuclear cell layer having a thickness 4.0 times the thickness of the mononuclear cell layer (upper layer having a thickness of 8.0 mm), and a subnatant directly below the mononuclear cell layer having a thickness 4.0 times the thickness of the mononuclear cell layer (lower layer having a thickness of 8.0 mm) were fractionated.

Example 2

The cell recovery ratio (%) was determined as in Example 1, except that the mononuclear cell layer, a supernatant (upper layer) directly above the mononuclear cell layer having a thickness 1.0 time the thickness of the mononuclear cell layer, and a subnatant (lower layer) directly below the mononuclear cell layer having a thickness 1.0 time the thickness of the mononuclear cell layer were fractionated.

Comparative Example 2

The cell recovery ratio (%) was determined as in Example 2, except that the centrifuge tube and pipette tips not coated with the poly MPC were used in the fractionation.

Example 3

The cell recovery ratio (%) was determined as in Example 1, except that the mononuclear cell layer, a supernatant (upper layer) directly above the mononuclear cell layer having a thickness of 5.0 mm, and a subnatant (lower layer) directly below the mononuclear cell layer having a thickness of 5.0 mm were fractionated.

Comparative Example 3

The cell recovery ratio (%) was determined as in Example 3, except that the centrifuge tube and pipette tips not coated with the poly MPC were used in the fractionation.

Example 4

The cell recovery ratio (%) was determined as in Example 1, except that the spiked blood was combined with RosetteSep Human CD45 Depletion Cocktail (STEM CELL Technologies, an antibody reagent for agglutinating red and white blood cells) in 1/20 the volume of the spiked blood, the mixture was left at room temperature for 20 minutes to cause agglutination, and the resulting mixture was diluted with an equal volume of a phosphate buffer solution to prepare a spiked blood dilution.

Comparative Example 4

The cell recovery ratio (%) was determined as in Example 4, except that the centrifuge tube and pipette tips not coated with the poly MPC were used in the fractionation.

Specific Cell-Capturing Method

Example A

Using azobisisobutyronitrile (AIBN), 2-methoxyethyl acrylate was thermally polymerized at 80° C. for six hours to produce poly(2-methoxyethyl acrylate) (molecular weight: Mn=about 15,000, Mw=about 50,000). Then, a 0.25% solution of the poly(2-methoxyethyl acrylate) in methanol was prepared.

The poly(2-methoxyethyl acrylate) solution (0.25% by mass) was injected into a glass chamber slide and dried to form a hydrophilic polymer layer.

Further, fibronectin was adsorbed onto the part coated with poly(2-methoxyethyl acrylate) (hydrophilic polymer layer). Specifically, a 200 µg/mL solution of fibronectin in a phosphate buffered saline (PBS) solution was prepared, injected, and left at 40° C. for one hour, followed by washing it with a PBS solution to prepare a medical analysis device.

Stained human colon adenocarcinoma (HT-29) cells were suspended in whole blood at a concentration of 100 cells per mL of blood to prepare spiked blood. The spiked blood was diluted with an equal volume of a phosphate buffer solution to prepare a spiked blood dilution. Next, a separation liquid (Lymphoprep, density=1.077±0.001 g/mL) was placed in a 15 mL centrifuge tube coated with a copolymer of MPC and butyl methacrylate (poly MPC: a polymer that hardly adsorbs proteins). Then, the spiked blood dilution was placed on the liquid, followed by centrifugation at 800 G for 20 minutes at room temperature (about 23° C.). Then, a mononuclear cell layer (fraction layer or line) was fractionated (collected). The inner surface of the pipette tips to be used to weigh, discharge, or inject the blood or solutions was coated with the poly MPC (a polymer that hardly adsorbs proteins). A phosphate buffer (PBS) solution was added to the fractionated (collected) solution, followed by centrifugation again to enrich the cells. After the centrifugation, aggregates at the lowermost layer were suspended in a liquid medium containing 10% fetal bovine serum (FBS) in a volume equal to the initial whole blood volume. A volume of 1 ml of the suspension was injected into the chamber and left at 37° C. for one hour to cause adhesion. Then, non-adhered cells were washed away with a PBS solution. The inner surface of the centrifuge tube and pipette tips to be used to centrifuge, weigh, discharge, or inject the solutions was coated with the poly MPC (a polymer that hardly adsorbs proteins). Next, the number of adhered cancer cells was counted using a fluorescence microscope. The ratio of the number of adhered cells to the initial number of cells was calculated to determine the cell capture ratio (%).

Example B

The cell capture ratio (%) was determined as in Example A, except that fibronectin was not adsorbed onto the hydrophilic polymer layer formed by injecting the poly(2-methoxyethyl acrylate) solution (0.25% by mass) into the glass chamber slide and drying it.

Example C

The cell capture ratio (%) was determined as in Example A, except that a poly(2-methoxyethyl acrylate) solution (0.35% by mass) was prepared and injected into the glass chamber slide.

Comparative Example A

The cell capture ratio (%) was determined as in Example A, except that the collected solution was changed to the collected solution fractionated/separated in Comparative Example a (specific cell-fractionating method).

Example 1

Using azobisisobutyronitrile (AIBN), 2-methoxyethyl acrylate was thermally polymerized at 80° C. for six hours to produce poly(2-methoxyethyl acrylate) (molecular weight: Mn=about 15,000, Mw=about 50,000). Then, a 0.25% solution of the poly(2-methoxyethyl acrylate) in methanol was prepared.

The poly(2-methoxyethyl acrylate) solution (0.25% by mass) was injected into a glass chamber slide and dried to prepare a medical analysis device.

A phosphate buffer (PBS) solution was added to the collected solution fractionated/separated in Example 1 (specific cell-fractionating method), followed by centrifugation again to enrich the cells. After the centrifugation, aggregates at the lowermost layer were suspended in a liquid medium containing 10% fetal bovine serum (FBS) in a volume equal to the initial whole blood volume. A volume of 1 ml of the suspension was injected into the chamber and left at 37° C. for one hour to cause adhesion. Then, non-adhered cells were washed away with a PBS solution. Next, the number of adhered cancer cells was counted using a fluorescence microscope. The ratio of the number of adhered cells to the initial number of cells was calculated to determine the cell capture ratio (%).

Comparative Example 1-1

The cell capture ratio (%) was determined as in Example 1, except that the collected solution was changed to the collected solution fractionated/separated in Comparative Example 1-1 (specific cell-fractionating method).

Comparative Example 1-2

The cell capture ratio (%) was determined as in Example 1, except that the collected solution was changed to the collected solution fractionated/separated in Comparative Example 1-2 (specific cell-fractionating method).

Comparative Example 1-3

The cell capture ratio (%) was determined as in Example 1, except that the collected solution was changed to the collected solution fractionated/separated in Comparative Example 1-3 (specific cell-fractionating method).

Example 2

The cell capture ratio (%) was determined as in Example 1, except that the collected solution was changed to the collected solution fractionated/separated in Example 2 (specific cell-fractionating method).

Comparative Example 2

The cell capture ratio (%) was determined as in Example 1, except that the collected solution was changed to the collected solution fractionated/separated in Comparative Example 2 (specific cell-fractionating method).

Example 3

The cell capture ratio (%) was determined as in Example 1, except that the collected solution was changed to the collected solution fractionated/separated in Example 3 (specific cell-fractionating method).

Comparative Example 3

The cell capture ratio (%) was determined as in Example 1, except that the collected solution was changed to the collected solution fractionated/separated in Comparative Example 3 (specific cell-fractionating method).

Example 4

The cell capture ratio (%) was determined as in Example 1, except that the collected solution was changed to the collected solution fractionated/separated in Example 4 (specific cell-fractionating method).

Comparative Example 4

The cell capture ratio (%) was determined as in Example 1, except that the collected solution was changed to the collected solution fractionated/separated in Comparative Example 4 (specific cell-fractionating method).

Comparative Example 5

A phosphate buffer (PBS) solution was added to the collected solution fractionated/separated as in Comparative Example 1-2 (specific cell-fractionating method), followed by centrifugation again to enrich the cells. After the centrifugation, aggregates at the lowermost layer were suspended in a liquid medium containing 10% fetal bovine serum (FBS) in a volume equal to the initial whole blood volume. A volume of 1 ml of the suspension was injected into a glass chamber slide not coated with poly(2-methoxyethyl acrylate), and left at 37° C. for one hour to cause adhesion. Then, non-adhered cells were washed away with a PBS solution. Next, the number of adhered cancer cells was counted using a fluorescence microscope. The ratio of the number of adhered cells to the initial number of cells was calculated to determine the cell capture ratio (%)

[Thickness of Hydrophilic Polymer Layer (Coating Layer)]

The thickness of the hydrophilic polymer layer of the medical analysis devices was determined by measuring (photographing) a cross section of the hydrophilic polymer layer using a TEM at an accelerating voltage of 15 kV and a magnification of 10,000 times.

[Contact Angle with Water]

A volume of 2 µL of distilled water was dropped onto the surface of the hydrophilic polymer layer of each medical analysis device. Thirty seconds later, the contact angle was measured by the θ/2 method at room temperature.

The centrifuge tube used in Example 4 was cut out to measure the contact angle of the inner surface, which was found to be 18.3 degrees.

TABLE 1

|  | Example a | Comparative Example a |
|---|---|---|
| Cell recovery ratio (%) | 90.0 | 72.2 |

TABLE 2

|  | Example A | Example B | Example C | Comparative Example A |
|---|---|---|---|---|
| Thickness (nm) of hydrophilic polymer layer (coating layer) | 142.5 | 142.5 | 236.2 | 142.5 |
| Contact angle (degrees) with water of hydrophilic polymer layer surface | 43.4 | 43.4 | 45.6 | 43.4 |
| Cell capture ratio (%) | 83 | 70 | 78 | 41 |

TABLE 3

|  | Example 1 | Example 2 | Example 3 | Example 4 |
|---|---|---|---|---|
| Thickness (nm) of hydrophilic polymer layer (coating layer) | 142.5 | 142.5 | 142.5 | 142.5 |
| Contact angle (degrees) with water of hydrophilic polymer layer surface | 43.4 | 43.4 | 43.4 | 43.4 |
| Cell recovery ratio (%) | 95.6 | 94.5 | 90.3 | 96.5 |
| Cell capture ratio (%) | 87 | 86 | 85 | 91 |

|  | Comparative Example 1-1 | Comparative Example 1-2 | Comparative Example 1-3 | Comparative Example 2 | Comparative Example 3 | Comparative Example 4 | Comparative Example 5 |
|---|---|---|---|---|---|---|---|
| Thickness (nm) of hydrophilic polymer layer (coating layer) | 142.5 | 142.5 | 142.5 | 142.5 | 142.5 | 142.5 | 0 |
| Contact angle (degrees) with water of hydrophilic polymer layer surface | 43.4 | 43.4 | 43.4 | 43.4 | 43.4 | 43.4 | — |
| Cell recovery ratio (%) | 80.3 | 68.4 | 81.5 | 76.2 | 79.8 | 86.7 | 68.4 |
| Cell capture ratio (%) | 72 | 60 | 65 | 68 | 71 | 79 | 49 |

The cell recovery ratio was increased when a blood or biological fluid sample was fractionated/separated by centrifugation using a container having a low protein adsorbing layer formed on the inner surface.

Further, when the fractionated and collected liquid was brought into contact with a hydrophilic polymer layer (coating layer), specific sells such as cancer cells were selectively captured, and the specific cell capture ratio was increased.

REFERENCE SIGNS LIST 11 centrifugal container
12 separation liquid
13 sample
14 fraction layer or line
15 upper layer (supernatant) above the fraction layer or line
16 lower layer (subnatant) below the fraction layer or line
17 red blood cell-containing layer
18 low protein adsorbing layer
2 multi-well plate
21 well
22 hydrophilic polymer layer

The invention claimed is:

1. A method for fractionating cancer cells present in blood or biological fluid, the method comprising fractionating the blood or biological fluid by centrifugation to collect the cancer cells in the blood or biological fluid,
wherein
the centrifugation is carried out using a container having a low protein adsorbing layer formed on at least a portion of an inner surface thereof, and
the low protein adsorbing layer is formed of a low protein adsorbing polymer produced by polymerizing a monomer composition containing at least one selected from the group consisting of an alkali metal-containing monomer, a zwitterionic monomer and a mixture thereof.

2. The method according to claim 1,
wherein the method comprises collecting a fraction layer as well as upper and lower layers, respectively, above and below the fraction layer formed by the fractionation by centrifugation, and
the upper and lower layers to be collected each have a thickness that is not more than 2.0 times the fraction layer thickness.

3. The method according to claim 1,
wherein the method comprises collecting a fraction line or layer as well as upper and lower layers respectively above and below the fraction line or layer formed by the fractionation by centrifugation, and
the upper and lower layers to be collected each have a thickness of 5.0 mm or less.

4. The method according to claim 1, wherein a separation liquid is present in the fractionation by centrifugation.

5. The method according to claim 4, wherein the separation liquid has a density of 1.060 to 1.115 g/mL.

6. The method according to claim 4, wherein the separation liquid has a density of 1.060 to 1.085 g/mL.

7. The method according to claim 1, wherein at least a portion of the inner surface of the container has a contact angle with water of 30 degrees or less.

8. The method according to claim 1, wherein the method comprises mixing the blood or biological fluid with a hemolytic agent, followed by the centrifugation.

9. The method according to claim 1, wherein the method comprises agglutinating blood cells in the blood or biological fluid, followed by the centrifugation.

10. A method for capturing cancer cells present in blood or biological fluid, the method comprising fractionating the blood or biological fluid by centrifugation to collect the cancer cells in the blood or biological fluid, and then capturing the cancer cells present in the collected liquid onto a hydrophilic polymer layer, wherein the centrifugation is carried out using a container having a low protein adsorbing layer formed on at least a portion of an inner surface thereof, the low protein adsorbing layer is formed of a low protein adsorbing polymer produced by polymerizing a monomer composition containing at least one selected from the group consisting of an alkali metal-containing monomer, a zwitterionic monomer and a mixture thereof.

11. The method according to claim 10, wherein the method comprises collecting a fraction layer as well as upper and lower layers, respectively, above and below the fraction layer formed by the fractionation by centrifugation, and then capturing the cancer cells present in the collected liquid onto a hydrophilic polymer layer, and the upper and lower layers to be collected each have a thickness that is not more than 2.0 times a thickness of the fraction layer.

12. The method according to claim 10, wherein the method comprises collecting a fraction line or layer as well as upper and lower layers, respectively, above and below the fraction line or layer formed by the fractionation by centrifugation, and then capturing the cancer cells present in the collected liquid onto a hydrophilic polymer layer, and the upper and lower layers to be collected each have a thickness of 5.0 mm or less.

13. The method according to claim 10, wherein a separation liquid is present in the fractionation by centrifugation.

14. The method according to claim 13, wherein the separation liquid has a density of 1.060 to 1.115 g/mL.

15. The method according to claim 13, wherein the separation liquid has a density of 1.060 to 1.085 g/mL.

16. The method according to claim 10, wherein at least a portion of the inner surface of the container has a contact angle with water of 30 degrees or less.

17. The method according to claim 10, wherein the method comprises mixing the blood or biological fluid with a hemolytic agent, followed by the centrifugation.

18. The method according to claim 10, wherein the method comprises agglutinating blood cells in the blood or biological fluid, followed by the centrifugation.

19. The method according to claim 10, wherein the method comprises diluting the blood or biological fluid and then agglutinating blood cells in the blood or biological fluid, followed by the centrifugation.

20. The method according to claim 10, wherein the method comprises agglutinating blood cells in the blood or biological fluid and then diluting the blood or biological fluid, followed by the centrifugation.

21. The method according to claim 18, wherein the step of agglutinating the blood cells comprises an antigen-antibody reaction.

22. The method according to claim 10, wherein the hydrophilic polymer layer is formed of at least one hydrophilic polymer selected from the group consisting of poly(meth)acryloylmorpholine and polymers represented by the following formula (I):

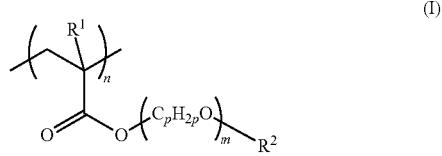

wherein
$R^1$ represents a hydrogen atom or a methyl group;
$R^2$ represents an alkyl group;
p represents 1 to 8; m represents 1 to 5; and n represents the number of repetitions.

23. The method according to claim 10, wherein the hydrophilic polymer layer is formed of a copolymer of at least one hydrophilic monomer selected from the group consisting of (meth)acryloylmorpholine and compounds represented by the following formula (II):

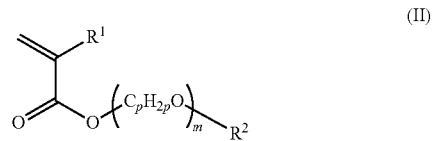

wherein
$R^1$ represents a hydrogen atom or a methyl group;
$R^2$ represents an alkyl group;
p represents 1 to 8; and m represents 1 to 5, with an additional monomer.

24. The method according to claim 10, wherein the hydrophilic polymer layer has a thickness of 10 to 800 nm.

25. The method according to claim 10, wherein fibronectin is adsorbed on a surface of the hydrophilic polymer layer.

26. The method according to claim 1, wherein the low protein adsorbing polymer is a copolymer of 2-(meth)acryloyloxyethyl phosphorylcholine and butyl methacrylate.

27. The method according to claim 10, wherein the low protein adsorbing polymer is a copolymer of 2-(meth)acryloyloxyethyl phosphorylcholine and butyl methacrylate.

* * * * *